US 6,718,581 B2
United States Patent
Riach

Patent No.: US 6,718,581 B2
Date of Patent: Apr. 13, 2004

(54) SUPPORT DEVICE

(75) Inventor: Jeffrey M. Riach, Cockeysville, MD (US)

(73) Assignee: Oakworks, Inc., New Freedom, PA (US)

( * ) Notice: Subject to any disclaimer, the term of this patent is extended or adjusted under 35 U.S.C. 154(b) by 0 days.

(21) Appl. No.: 10/122,391

(22) Filed: Apr. 16, 2002

(65) Prior Publication Data

US 2002/0184706 A1 Dec. 12, 2002

Related U.S. Application Data

(60) Provisional application No. 60/295,815, filed on Jun. 6, 2001.

(51) Int. Cl.[7] .................. A61G 13/12; A47C 20/04
(52) U.S. Cl. .................. 5/632; 5/640; 5/607
(58) Field of Search .......... 5/632, 630, 636, 5/638, 640, 643, 657, 622, 727, 731, 733, 735, 740, 655.9, 953

(56) References Cited

U.S. PATENT DOCUMENTS

| 1,632,160 | A | * | 6/1927 | Barnes | 27/13 |
| 2,099,977 | A | * | 11/1937 | Harris | 5/630 X |
| 2,470,398 | A | * | 5/1949 | Hayes | 5/632 X |
| 3,828,377 | A | * | 8/1974 | Eary, Sr. | 5/632 |
| 3,843,980 | A | * | 10/1974 | Rodriguez | 5/733 |
| 4,398,707 | A | * | 8/1983 | Cloward | 5/632 |
| 4,441,221 | A | * | 4/1984 | Enste et al. | 5/657 |
| 4,596,384 | A | * | 6/1986 | Blosser | 5/638 X |
| 4,840,362 | A | * | 6/1989 | Bremer et al. | 5/632 |
| 4,923,187 | A | | 5/1990 | Mombrinie | |
| 5,009,407 | A | * | 4/1991 | Watanabe | 5/618 |
| 5,014,375 | A | * | 5/1991 | Coonrad et al. | 5/648 |
| 5,177,823 | A | | 1/1993 | Riach | 5/636 |
| 5,401,078 | A | | 3/1995 | Riach | 297/423.11 |
| 5,448,790 | A | * | 9/1995 | Saro et al. | 5/657 |
| 5,661,860 | A | * | 9/1997 | Heitz | 5/632 |
| 5,778,887 | A | | 7/1998 | Curtiss | |
| 5,784,734 | A | | 7/1998 | Scott et al. | |
| 5,893,183 | A | * | 4/1999 | Bechtold, Jr. | 5/632 |
| 5,987,675 | A | * | 11/1999 | Kim | 5/632 |
| 6,047,420 | A | * | 4/2000 | Priester, III et al. | 5/632 |
| 6,138,304 | A | * | 10/2000 | Lipsky et al. | 5/622 X |
| 6,154,903 | A | * | 12/2000 | Wai-Chung | 5/632 |
| 6,397,414 | B1 | * | 6/2002 | Lloyd | 5/622 |
| 2002/0184706 | A1 | * | 12/2002 | Riach | 5/632 |

FOREIGN PATENT DOCUMENTS

| EP | 0 655 211 A1 | | 5/1995 | | |
| FR | 1464661 | | 3/1967 | | |
| FR | 2661602 A1 | * | 11/1991 | | 5/630 |
| GB | 2192785 A | * | 1/1988 | | 5/630 |
| GB | 2314506 A | * | 1/1998 | | 5/630 |

* cited by examiner

Primary Examiner—Robert G. Santos
(74) Attorney, Agent, or Firm—Nixon Peabody LLP; Daniel S. Song

(57) ABSTRACT

A support device having a substantially rigid support plate, a headrest supported on the support plate, the headrest being adapted to support the user's head, and a support pad at least partially supported on the support plate, the support pad being adapted to support the user's torso. In addition, a support pad for supporting torso of a user with enhanced comfort is provided, the support pad including a center pad, two side pads, and a stomach pad where the center pad has a durometer/compliance which is stiffer than the two side pads.

29 Claims, 5 Drawing Sheets

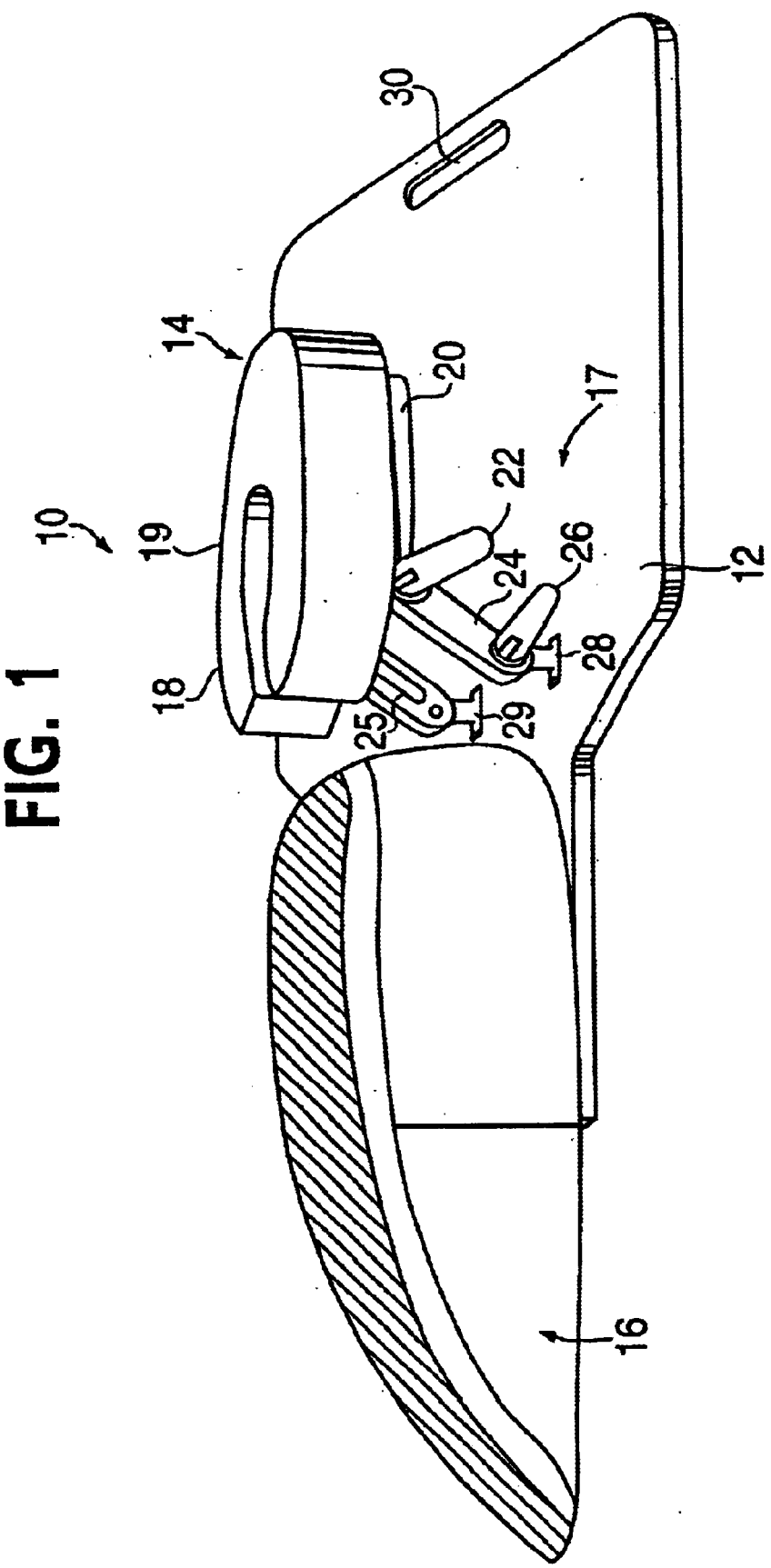

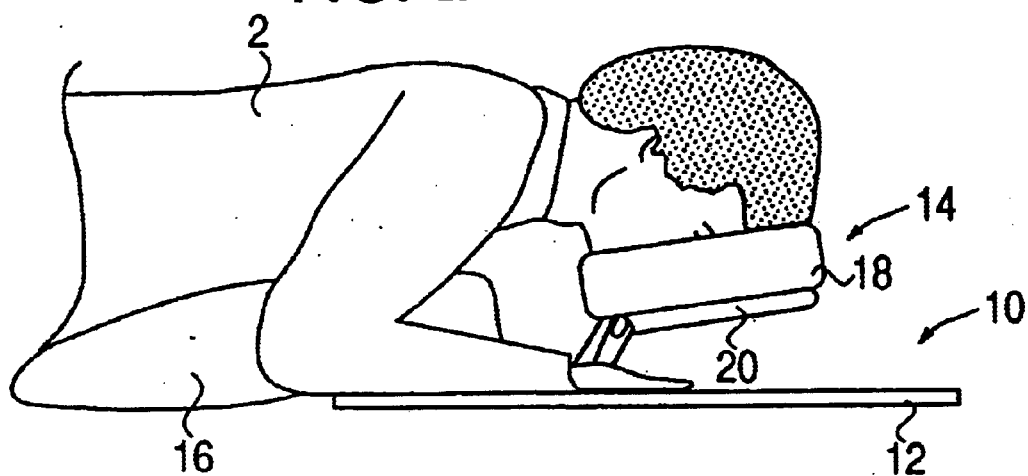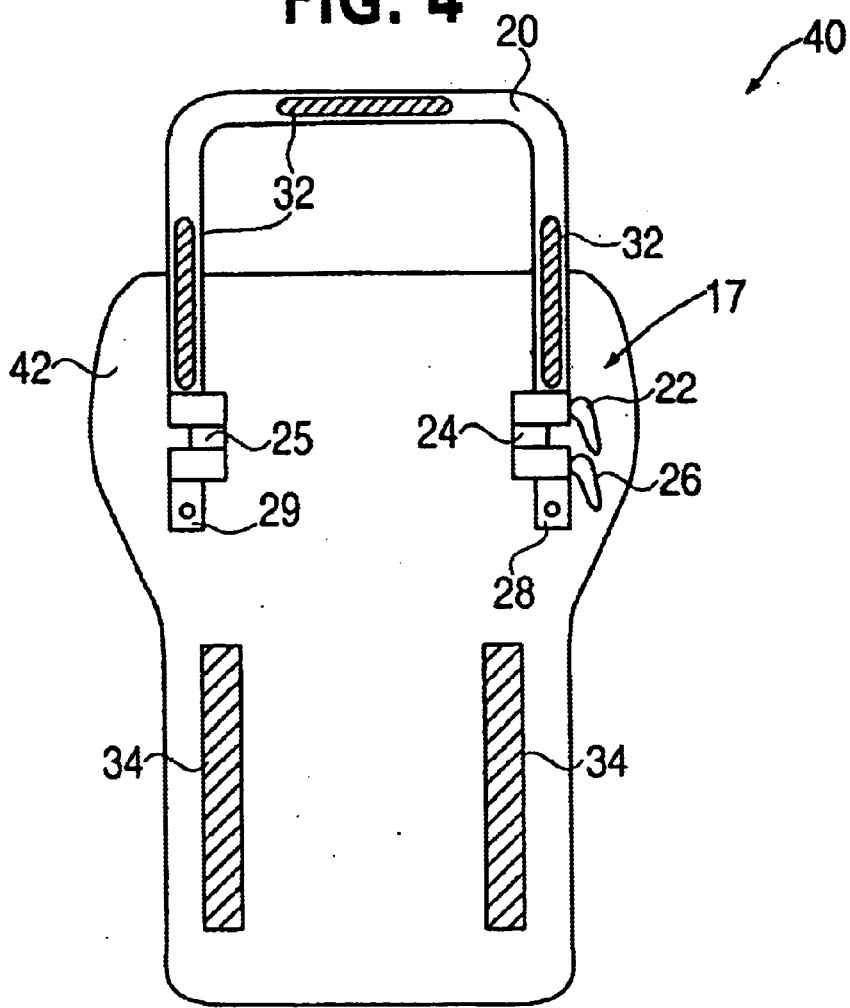

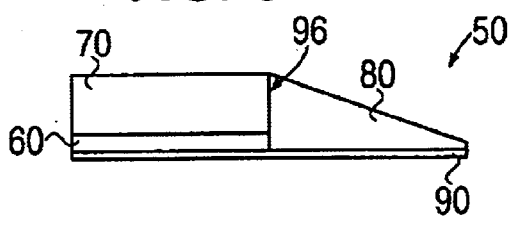
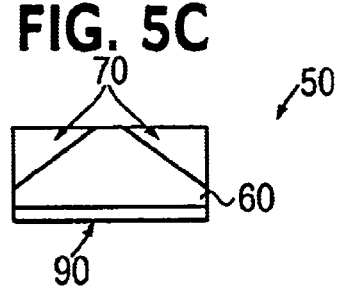
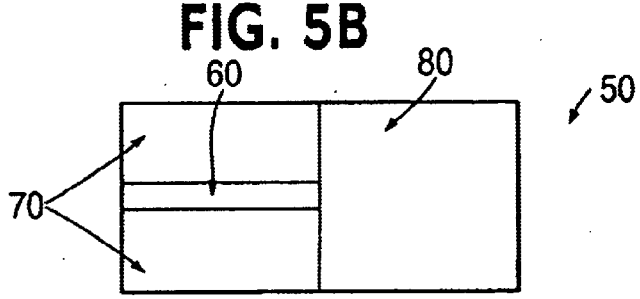
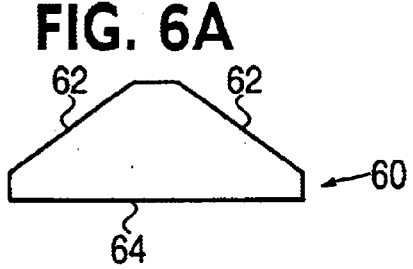
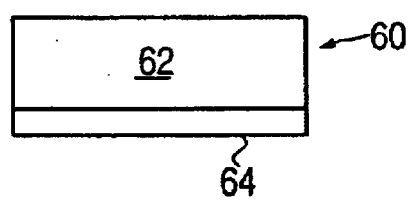
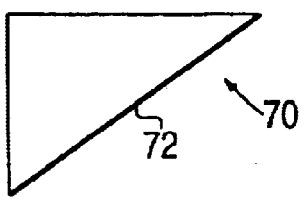
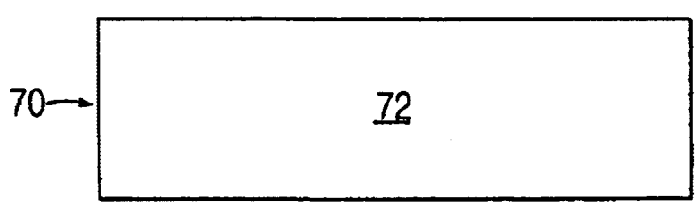

SUPPORT DEVICE

This application claims priority to U.S. Provisional Application Ser. No. 60/295,815 filed Jun. 6, 2001.

BACKGROUND OF THE INVENTION

1. Field of the Invention

The present invention is directed to support devices for use in treating patients. More specifically, the present invention is directed to such support devices which support the torso and/or the head of the patient.

2. Description of Related Art

In the fields of radiology and surgery there has been no product to allow a patient to lie face down for extended periods of time in relative comfort, to allow a practitioner such as a doctor or technician to accurately position the head and spine of the patient, and offer good radiolucency for better viewing of internal structures when x-rays are taken. Patients are typically asked to lie face down for extended periods with their heads turned to one side which is generally uncomfortable.

Some products are designed to more comfortably position the patients, but lack sufficient air flow or the ability to lower the shoulders out of the path of the x-rays. This lowers the image quality and adversely affects the practitioner's ability to see the internal structures well. These products also do not offer firm enough vertical support to the patient so that during procedures that require application of moderate vertical pressure on the patient, the patient is readily displaced downward thus making the practitioner's task more difficult.

SUMMARY OF THE INVENTION

In view of the foregoing, it is an object of the present invention to provide an improved support device which avoids the limitations of the prior art. In this regard, one embodiment of the present invention supports patients in a way which supports comfortable breathing through superior airflow around the face and minimizes post surgical soft tissue complications caused by extended periods of uncomfortable positioning. This embodiment also minimizes the degradation of x-ray images associated with other devices presently on the market by extensively using radiolucent materials and by allowing the patient to position the arms and shoulders out of the way of the x-ray. In one embodiment of the present invention, multitude of cervical positioning options for patients is made possible and in addition, height of the pad of the head support is also adjustable to give the practitioner more options for arm positioning. This increases the quality of lateral views of the spine, which presently are of poor quality due to the inability to lower the shoulders out of the way.

The above noted advantages and others are attained by a support device in accordance with one embodiment of the present invention including a substantially rigid support plate, a headrest supported on the support plate, the headrest being adapted to support the user's head, and a support pad at least partially supported on the support plate, the support pad being adapted to support the user's torso. In accordance with one embodiment, the support plate includes at least one hand support region and is made of a substantially radiolucent material.

In another embodiment, the headrest includes a headrest pad which is made of a substantially radiolucent material. The headrest of one embodiment is supported on the support plate by an articulating support assembly that allows articulation of the headrest relative to the support plate, the articulating support assembly being preferably made of a substantially radiolucent material. In one preferred embodiment, the articulating support assembly includes a support member that is lockably secured to a first support rod via a first lock lever, the first support rod being lockably secured to a mounting post secured to the support plate via a second lock lever.

In accordance with another aspect of the present invention, a support pad for supporting torso of a user with enhanced comfort is provided, the support pad including a center pad, two side pads, and a stomach pad where the center pad has a durometer/compliance which is stiffer than the two side pads. In this regard, in another embodiment, the stomach pad has a durometer/compliance which is substantially the same as that of the center pad and the plurality of separate pads are joined together. In addition, the support pad may also include a bottom pad.

In accordance with one embodiment, the center pad has a substantially triangular cross sectional profile with sloped surfaces and the two side pads each have substantially triangular cross sectional profile with at least one sloped surface which are adhered to the sloped surfaces of the center pad. In addition, the stomach pad preferably has a wedge shape having an inclined surface which is angled approximately 20 degrees.

These and other objects, features and advantages of the present invention will become more apparent from the following detailed description of the preferred embodiments of the present invention when viewed in conjunction with the accompanying drawings.

BRIEF DESCRIPTION OF THE DRAWINGS

FIG. 1 is a perspective view of the support device in accordance with one embodiment of the present invention.

FIG. 2 is the support device of FIG. 1 in use by a patient.

FIG. 4 is a top view of a support device in accordance with yet another embodiment of the present invention without the hand rest portion.

FIGS. 5A–5C each show various views of the foam subassembly used in the torso cushion in accordance with one embodiment of the present invention.

FIGS. 6A–6B each show views of the center pad of the foam subassembly.

FIGS. 7A–7B each show a view of one of the side pads of the foam subassembly.

DETAILED DESCRIPTION OF THE PREFERRED EMBODIMENT

Figure 3:
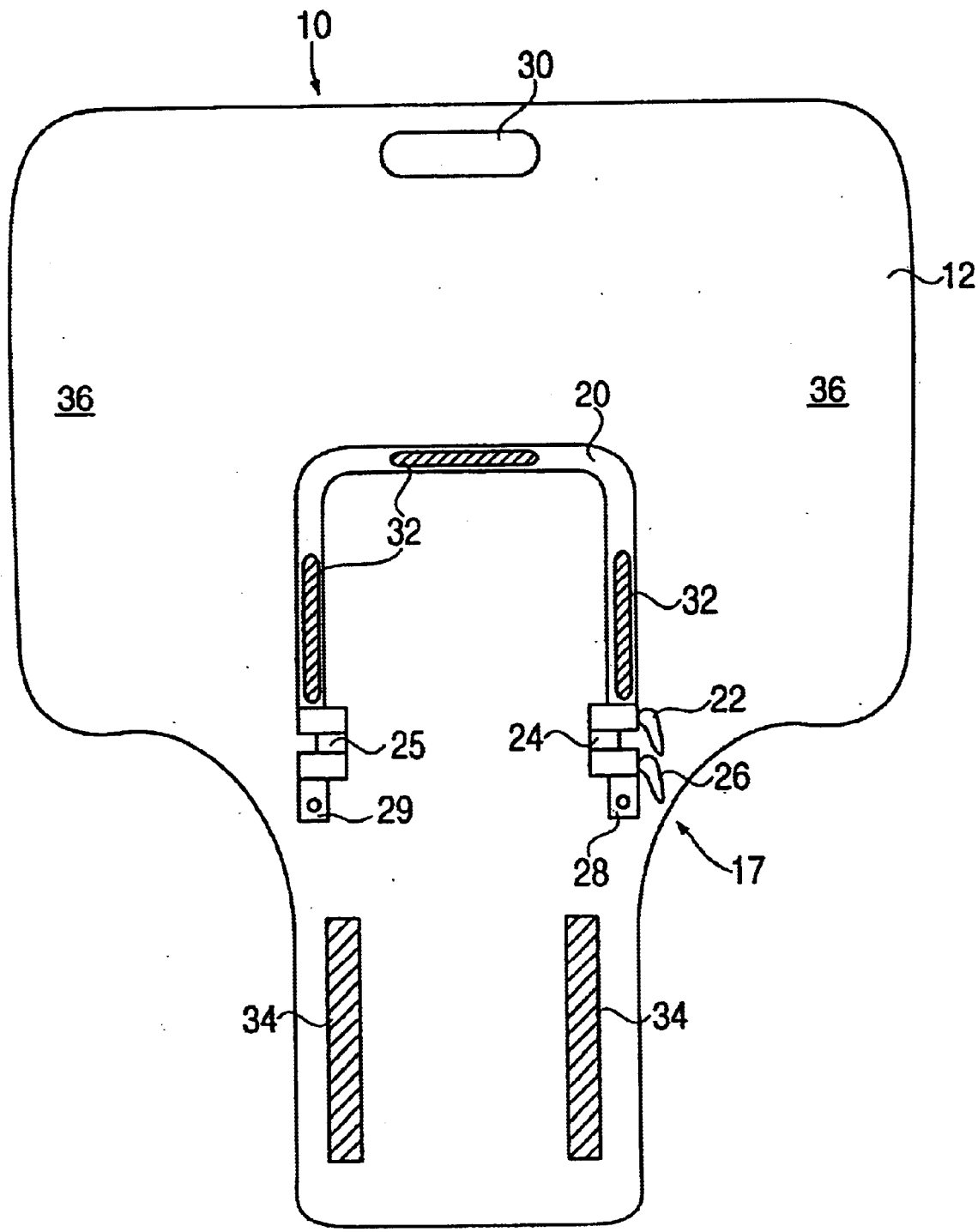
FIG. 3 is a top view of the support device of FIG. 1 with the stomach pad and the head pad removed.

FIG. 1 shows a support device 10 in accordance with one preferred embodiment of the present invention which may be used to provide comfortable torso and head support to a user such as a patient. It should initially be noted that whereas one preferred embodiment of the present invention is described in detail below, the present invention is not limited thereto.

As can be seen, the present embodiment of the support device 10 includes a support plate 12 made of a substantially rigid material. As can be seen in FIG. 1, the headrest 14 includes a headrest pad 18 that is supported by support member 20, the headrest pad 18 being made of polyurethane and/or polyethylene foam which is also substantially radiolucent. The head rest 14 of the illustrated embodiment is supported on the support plate 12 by an articulating support assembly 17 that allows articulation of the headrest 14 relative to the support plate 12. In this regard, the support member 20 is lockably secured at least at one end via first lock lever 22 to first support rod 24, the other end of the support member (shown in FIG. 3) being pivotably secured to the second support rod 25. The first support rod 24 is in turn, lockably supported by second lock lever 26 to the first mounting post 28 while the second support rod 25 is pivotably secured to the second mounting post 29, both the first mounting post 28 and the second mounting post 29 being secured to the support plate 12. The support plate 12 may be provided with a handle opening 30 to facilitate transport of the support device 10.

The support plate 12 as well as the various components of the headrest 14 and the support assembly 17 including the support member 20, the support rods 24, 25, the lock levers 22, 26 as well as the mounting posts 28, 29 are preferably made of radiolucent (i.e. substantially transparent to x-rays) materials such as polycarbonate, Lexan, Plexiglas, Kevlar, carbon fiber, or fiberglass to minimize interference to x-rays. A significant advantage of this is that in applications where x-rays are taken of the user supported in a prone position on the support device 10, the resulting x-ray images are clear and easy to read. Of course, other substantially radiolucent materials can also be used. In other instances, aluminum tubing may be used for one or more of these components to reduce material and manufacturing costs. Although aluminum is not fully radiolucent, it is substantially radiolucent so that sufficiently clear x-rays can be obtained. Furthermore, various components such as fasteners that secure the mounting posts 28, 29 may be conventional fasteners to further minimize costs. Although such fasteners would not be radiolucent, these components are relatively small and should not significantly impede obtaining of x-rays. Moreover, it should be made clear that the presently described embodiment of the support device in accordance with the present invention is made to be substantially radiolucent so that it can be readily used for treating patients, it should be noted that the radiolucency is not required to practice the present invention. In other applications such as massage services, radiolucency would not be a requirement and thus, the various components may be made from conventional materials that are not radiolucent. However, as can be appreciated, such radiolucency provides additional functionality to the present invention in allowing the obtaining of substantially clear and unobstructed x-rays.

As can be seen in FIG. 2, the support device 10 in accordance with the present invention allows the user 2 to be supported in a prone position wherein the user's head is supported by the headrest pad 18 while the user's torso is supported by the support pad 16. In the present embodiment, both the headrest pad 18 and the support pad 16 are made of polyurethane and/or polyethylene which are both substantially radiolucent so as to minimize interference with x-rays. Of course, the headrest pad 18 and the support pad 18 may be covered with a durable covering as well. The head pad 18 is designed with an opening 19 to allow comfortable support of the user's 2 face, when the user 2 is lying in the prone position.

FIG. 3 shows an enlarged topographical view of the support plate 12 with the headrest pad 18 and the support pad 16 removed. As can be seen, the support member 20 is U-shaped in the present embodiment with two ends that are connected to the support rods 24, 25 as described above. The support rods 24, 25 are in turn, secured to the support plate 12 by the mounting posts 28, 29. As previously described, one end of the support member 20 is lockably secured to the first support rod 24 by the first lock lever 22. This assembly in turn, is lockably connected to the first mounting posts 28 by the lock lever 26. The use of the first and second lock levers 22 and 26 respectively allows the headrest pad 18 to be articulated in various directions to adjust for the height and angle as well as the lateral position relative to the support plate 12. The general details of such lock levers are known in the art and need not be discussed in further detail here. Of course, whereas in the present embodiment, the second support rod 25 is not provided with any lock levers, in other embodiments, it may likewise be provided with lock levers as well to allow lockable adjustment of its position. Moreover, the headrest 14 may also be provided with a double locking mechanism as described in the U.S. Pat. No. 5,177,823 issued to the present applicants which is incorporated herein by reference.

FIG. 3 also shows that the support member 20 maybe provided with securement strips 32 that secure the headrest pad 18 in place. For instance, the securement strips 32 may be Velcro strips that allow attachment and detachment of the headrest pad 18. In a similar manner, FIG. 3 also shows securement strips 34 that allow removable securement of the support pad 16 in the manner shown in FIG. 1.

As can also be seen in FIGS. 2 and 3, the support device 10 in accordance with the illustrated embodiment further provides a hand support region 36 (FIG. 3) on the support plate 12 for allowing the user to comfortably place his/her hand in the manner shown in FIG. 2. FIG. 4 shows another embodiment of the support device 40 in accordance with the present invention in which the support plate 42 does not include the hand support region of the embodiment shown in FIG. 3. This embodiment of FIG. 4 may be used in those instances where the patient is already lying on a flat table that allows the user's hands to be supported on the table surface. It should be evident that the embodiment of FIG. 4 otherwise incorporates all of the features of the support device of FIG. 3 and these common features have been enumerated using the same numerals. Consequently, the details of this embodiment are omitted to avoid repetition.

FIGS. 5A–5C each show various views of the foam subassembly 50 used for the support pad 16 which may be secured to the support plate 20 in the manner described above. In this regard, as previously noted, the foam subassembly 50 is preferably radiolucent and may be made from polyurethane and/or polyethylene foam which is covered with a protective cover such as vinyl or other appropriate covering material. As can be seen, the foam subassembly 50 includes various components including center pad 60, side pads 70, stomach pad 80 and bottom pad 90 which is only visible in FIGS. 5A and 5C. Each of these pads are preferably radiolucent and are assembled in a manner to provide the foam subassembly 50 as shown in FIGS. 5A–5C. In this regard, the joining interfaces of these pads may be provided with glue 96, other adhesive or other joining mechanism to secure the pads together. As will be explained in further detail hereinbelow, the provisions of the foam subassembly 50 having multiple pads as shown is especially advantageous in providing a comfortable support pad which will allow the user's shoulders to drop toward the support plate 12 while providing adequate support to the user's torso thereby facilitating obtaining of clear, unobstructed x-rays and also facilitating treatment of the patient by the practitioner such as a doctor.

An enlarged view of the center pad 60 is shown in FIGS. 6A—6A. As can be seen in FIG. 6A, the center pad 60 has a generally triangular cross sectional profile with sloped surfaces 62. FIG. 6b shows a side profile of the center pad 60. The bottom surface 64 of the center pad 60 is secured toward one end of the bottom pad 90 as evident in FIGS. 5A–5C. FIGS. 7A and 7B show one side pad 70 that is adapted to be adhered to one of the sloped surfaces 62 of the center pad 60. As can be seen, the side pad 70 also has a triangular cross sectional profile as most clearly shown in FIG. 7A, the sloped surface 72 being sloped to correspondingly mate to one of the sloped surfaces 62 of the center pad 60. FIG. 7b shows the side profile of the side pad 70. It should also be noted that whereas only one side pad 70 is shown in FIGS. 7A–7B, another side pad as shown in FIGS. 5B and 5C would be shaped in a mirror image of the side pad 70 shown in FIG. 7A and adhere to the other sloped surface 62 of the center pad 60.

Figure 8A:
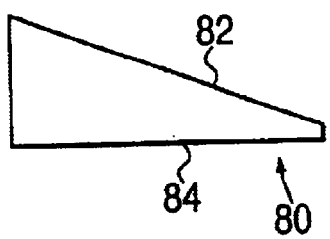
FIGS. 8A–8B each show views of the stomach pad of the foam subassembly.
Figure 8B:
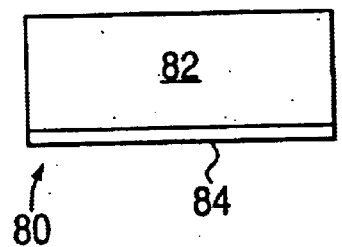
Figure 9A:
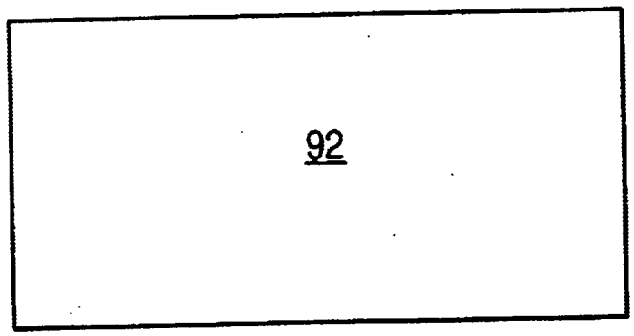
FIGS. 9A–9B show views of the bottom pad of the foam subassembly.
Figure 9B:
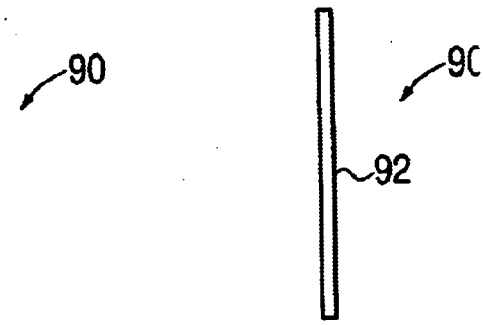

FIGS. 8A–8B each show various views of the stomach pad 80 used to form the foam subassembly 50 of FIGS. 5A–5B. As can be seen, the stomach pad 80 is wedge shaped as can be seen most clearly in the side profile view of FIG. 8A. FIG. 8b shows the end view of the stomach pad 80. The stomach pad 80 may be angled at approximately 20 degrees thereby providing a gradual inclined surface 82 to enhance the comfort of the user. Of course in other embodiments, different incline angles may be used. The bottom surface 84 of the stomach pad 80 is secured toward the other end of the bottom pad 90 which is more clearly shown in FIGS. 9A–9B. The bottom pad 90 may be used to more firmly support the various pads described above. In this regard, the bottom pad 90 provides a flat surface 92 to which the center pad 60 and the stomach pad 80 is adhered in the manner shown in FIGS. 5A–5C.

In the preferred embodiment, the bottom pad 90 is relatively stiffer than the other various pads to provide a relatively stiff and yet compliant support of the pads that are adhered thereto. In addition, the stomach pad 80 as well as the center pad 60 are preferably made to have similar durometer/compliance which is stiffer than the two side pads 70. The side pads 70 are made relatively soft as compared to the other pads so that when in use, the user's shoulders can be lowered to a more comfortable prone position which also allows obtaining of more unobstructed x-rays. Moreover, the harder durometer center pad 60 and the stomach pad 80 ensures proper support of the cervical and abdominal regions so that significant pressures can be applied to the spine or the areas near the spine by the practitioner treating the patient or other user of the support device 10. Preferably, in the illustrated embodiment, the bottom pad 90 is stiff enough to allow elevation or upward propping of the support pad 16 by placing an object underneath the support pad 16 without causing discomfort to the patient or user of the support device 10. For instance, two small support pads (not shown) about 1 inch thick may be provided with the support device 10 so that the support pad 16 may be propped upward using one of the support pads or both support pads stacked on top of each other.

Of course, it should be evident that the specific dimensions of the foam subassembly 50 and the various components including center pad 60, side pads 70, stomach pad 80 and bottom pad 90 may be determined and selected by considering the anticipated user's body dimensions and proportions. In this regard, suitable dimensions for these components have been determined by considering body dimensions and proportions of a typical person. In particular, the center pad may have a height of approximately 4.5 inches and be approximately 11 inches in width and depth. The sloped surfaces 62 of the center pad 60 may be approximately 37 degrees. Each of the side pads 70 may have a height of approximately 3.5 inches, a width of approximately 4.75 inches, and a depth of approximately 11 inches, the sloped surface 72 corresponding to the sloped surfaces 62 of the center pad 60. The stomach pad may have a height of approximately 4.5 inches, and width and depth of approximately 11 inches, the inclined surface 82 being angled at approximately 20 degrees. Lastly, the optional bottom pad 90 may be approximately 0.5 inch in height, approximately 11 inches in width, and approximately 22 inches in depth. Again, these dimensions are only provided as an example and different dimensions may also be used.

Thus, in accordance with the above discussed embodiment of the present invention, the present support pad 16 allows the shoulders to round forward and out of the way of lateral views of any x-rays taken of the patient using the support device 10. By providing a support pad 16 with multiple components, i.e. various separate pads having different stiffness, a firm, relatively non-compressible support for the bony structure of the patient may be attained to minimize movement during procedures involving considerable vertical pressure. In addition, softer, more comfortable pads can be used to allow the softer tissues to not experience too much pressure and to facilitate movement of the diaphragm for more comfortable respiration when in the prone position.

Furthermore, as also described previously, the headrest 14 offers both anterior/posterior positioning and cervical flexion to allow better visualization and patient positioning for treatment and x-rays. The shape of the support member 20 and the corresponding head pad 18 offers better air circulation to facilitate respiration. Moreover, this is attained with minimal x-ray opaque elements transversing the spine on anterior/posterior images so that any x-ray images obtained will be clear and largely unobstructed.

Again, it should be made clear that the presently described embodiment of the support device is made to be substantially radiolucent so that it can be readily used for treating patients. However, it is noted again that radiolucency is not required to practice the present invention. As previously described, in other applications such as massage services, radiolucency would not be a requirement and thus, the various components may be made from conventional materials that are not radiolucent. However, such radiolucency provides additional functionality to the present invention in allowing the obtaining of substantially clear and unobstructed x-rays.

While various embodiments in accordance with the present invention have been shown and described, it is understood that the invention is not limited thereto. The present invention may be changed, modified and further applied by those skilled in the art. Therefore, this invention is not limited to the detail shown and described previously, but also includes all such changes and modifications.

I claim:

1. A support device for facilitating positioning and enhance comfort of a user, said support device comprising:
   a substantially rigid support plate;
   a headrest supported on said support plate, said headrest being adapted to support the user's head; and
   a support pad at least partially supported on said support plate, said support pad being adapted to support the user's torso and comprises a foam subassembly having a plurality of separate pads;

wherein said headrest is supported on said support plate by an articulating support assembly that allows articulation of said headrest relative to said support plate, said articulating support assembly comprising a support member, at least one lock lever, and at least one support rod that is pivotably secured to a mounting post secured to said support plate.

2. The support device of claim 1, wherein said support plate includes at least one hand support region.

3. The support device of claim 1, wherein said support plate includes hook and loop fastener strips for removably securing said support pad.

4. The support device of claim 1, wherein said support plate is made of a substantially radiolucent material.

5. The support device of claim 4, wherein said radiolucent material is at least one of aluminum and alloys thereof, polycarbonate, polycarbonate resin, acrylic, aromatic polyamide fiber, carbon fiber, or fiberglass.

6. The support device of claim 1, wherein said headrest includes a headrest pad.

7. The support device of claim 6, wherein said headrest pad is made of a substantially radiolucent material.

8. The support device of claim 1, wherein said articulating support assembly is made of a substantially radiolucent material.

9. The support device of claim 8, wherein said radiolucent material is at least one of aluminum and alloys thereof, polycarbonate, polycarbonate resin, acrylic, aromatic polyamide fiber, carbon fiber, or fiberglass.

10. The support device of claim 1, wherein said at least one lock lever includes a first lock lever and a second lock lever.

11. The support device of claim 10, wherein said support member is lockably secured to said first support rod via said first lock lever, said first support rod being lockably secured to said mounting post via said second lock lever.

12. The support device of claim 1, wherein said plurality of separate pads includes a center pad, two side pads and a stomach pad.

13. The support device of claim 12, wherein said center pad has a durometer/compliance which is stiffer than said two side pads.

14. The support device of claim 13, wherein said stomach pad has a durometer/compliance which is substantially the same as that of said center pad.

15. The support device of claim 12, wherein said stomach pad has a durometer/compliance which is stiffer than said two side pads.

16. The support device of claim 12, wherein said plurality of separate pads are joined together.

17. The support device of claim 12, wherein said plurality of separate pads further includes a bottom pad.

18. The support device of claim 1, wherein said plurality of separate pads includes two side pads that each have substantially triangular cross sectional profile with at least one sloped surface.

19. The support device of claim 1, wherein said plurality of separate pads includes a stomach pad having a wedge shape with an inclined surface.

20. The support device of claim 19, wherein said inclined surface is angled approximately 20 degrees.

21. The support device for facilitating positioning and enhance comfort of a user, said support device comprising:
a substantially rigid support plate;
a headrest supported on said support plate, said headrest being adapted to support the user's head; and
a support pad at least partially supported on said support plate, said support pad being adapted to support the user's torso;
wherein said support pad further comprises a foam subassembly having a plurality of separate pads and said plurality of separate pads includes a center pad that has a substantially triangular cross sectional profile with sloped surfaces.

22. A support pad for supporting torso of a user with enhanced comfort, said support pad comprising:
a center pad defining an elongated support region positioned longitudinally along the support pad to support a chest of the user;
two side pads positioned longitudinally adjacent to said center pad; and
a stomach pad;
wherein said center pad has a durometer/compliance which is stiffer than said two side pads.

23. The support pad of claim 22, wherein said stomach pad has a durometer/compliance which is substantially the same as that of said center pad.

24. The support pad of claim 22, wherein said plurality of separate pads are joined together.

25. The support pad of claim 22, further comprising a bottom pad.

26. The support pad of claim 22, wherein said two side pads each have substantially triangular cross sectional profile with at least one sloped surface.

27. The support pad of claim 22, wherein said stomach pad has a wedge shape having an inclined surface.

28. The support pad of claim 27, wherein said inclined surface is angled approximately 20 degrees.

29. The support pad for supporting torso of a user with enhanced comfort, said support pad comprising:
a center pad;
two side pads; and
a stomach pad;
wherein said center pad has a durometer/compliance which is stiffer than said two side pads, and said center pad has a substantially triangular cross sectional profile with sloped surfaces.

* * * * *